(12) United States Patent
Brinz

(10) Patent No.: US 7,113,264 B2
(45) Date of Patent: Sep. 26, 2006

(54) APPARATUS AND METHOD FOR TESTING A MATERIAL

(75) Inventor: Thomas Brinz, Bissingen Unter der Teck (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/167,512

(22) Filed: Jun. 12, 2002

(65) Prior Publication Data

US 2003/0025898 A1    Feb. 6, 2003

(30) Foreign Application Priority Data

Jun. 12, 2001    (DE) ................ 101 28 449

(51) Int. Cl.
  *G01N 21/00* (2006.01)
(52) U.S. Cl. ........................................ 356/72
(58) Field of Classification Search ............... 356/72, 356/445, 73, 73.1; 324/753
  See application file for complete search history.

(56) References Cited

U.S. PATENT DOCUMENTS

| 3,401,589 | A | * | 9/1968 | Druschel et al. ............... 356/72 |
| 3,421,079 | A | * | 1/1969 | Ashley et al. ................. 356/72 |
| 3,443,214 | A | * | 5/1969 | Meservey ..................... 356/72 |
| 3,807,860 | A | * | 4/1974 | Brainard, II .................. 356/73 |
| 4,564,808 | A | * | 1/1986 | Faughnan et al. ........... 324/766 |
| 5,344,754 | A |   | 9/1994 | Zweig |
| 5,379,102 | A | * | 1/1995 | Takeuchi ...................... 356/72 |
| 5,568,252 | A | * | 10/1996 | Kusuda et al. ................. 356/72 |
| 5,570,175 | A | * | 10/1996 | Dobele et al. ................. 356/72 |
| 5,844,249 | A | * | 12/1998 | Takano et al. ............ 356/237.1 |
| 6,026,323 | A |   | 2/2000 | Skladnev et al. |
| 6,055,044 | A | * | 4/2000 | Uchiyama et al. .......... 356/73.1 |
| 6,157,449 | A | * | 12/2000 | Hajduk ....................... 356/367 |
| 6,228,652 | B1 |   | 5/2001 | Rodriguez et al. |
| 6,421,124 | B1 | * | 7/2002 | Matsumoto et al. ......... 356/401 |
| 6,462,817 | B1 | * | 10/2002 | Strocchia-Rivera ......... 356/369 |
| 6,511,854 | B1 | * | 1/2003 | Asanov et al. .............. 356/300 |
| 6,525,807 | B1 | * | 2/2003 | Morikawa et al. ............ 356/72 |
| 6,573,497 | B1 | * | 6/2003 | Rangarajan et al. ........ 250/306 |
| 6,594,012 | B1 | * | 7/2003 | Takeuchi et al. ............ 356/394 |
| 2003/0035109 | A1 | * | 2/2003 | Hartwich et al. ............. 356/72 |

FOREIGN PATENT DOCUMENTS

| DE | 279 952 | 6/1990 |
| DE | 4400689 | 7/1995 |
| DE | 19701904 | 7/1998 |
| GB | 2 047 884 | 12/1980 |
| GB | 2 174 800 | 11/1986 |
| JP | 8145894 | 6/1996 |
| JP | 11148919 | 6/1999 |
| SU | 1467404 | 3/1989 |
| WO | WO 91/08472 | 6/1991 |
| WO | WO 96/14569 | 5/1996 |

* cited by examiner

*Primary Examiner*—Layla G. Lauchman
*Assistant Examiner*—Juan D. Valentin, II
(74) *Attorney, Agent, or Firm*—Kenyon & Kenyon LLP

(57) ABSTRACT

An apparatus for testing a material (2), having a measurement unit for measuring at least one electrical parameter of the material (2) to be tested, is proposed that ensures a measuring of all relevant parameters of the material (2) under identical measurement conditions. According to the present invention, this is achieved in that an optical measurement apparatus is provided for the simultaneous measurement of at least one optical parameter of the material (2) to be tested.

23 Claims, 1 Drawing Sheet

APPARATUS AND METHOD FOR TESTING A MATERIAL

FIELD OF THE INVENTION

The invention relates to an apparatus and a method for testing a material.

BACKGROUND INFORMATION

Sensor materials that modify both an optical and electrical material parameter on the basis of a modification of a relevant environmental parameter may be required in at least some applications. For example, in $CO_2$ sensors made of soft polymers having a colorant and an auxiliary base, both the color and the conductivity of the pH indicator may be modified.

In combinatorial chemistry, in which, for example, a large number of varying samples, possibly having slightly varying compositions, are to be examined, corresponding materials may be examined electrically or optically independently of one another. For example, corresponding material samples may be charged with carbon dioxide ($CO_2$), while an electrical or optical parameter of the sample is measured.

Through the effect of the relevant environmental parameter, the material to be tested changes due to chemical conversions during the first measurement, for example, of the electrical parameter. This chemical conversion may falsify a subsequent second measurement, or prevent the subsequent measurement, for example, the optical measurement of an optical parameter of the material to be tested, from being performed using the same sample.

Thus, it is believed to be disadvantageous in that the measurement of the relevant parameters of the same sample may not be performed under identical measurement conditions.

SUMMARY OF THE INVENTION

An object of an exemplary embodiment according to the present invention is to provide an apparatus for testing a material, having a measurement unit for the measurement of at least one electrical parameter of the material, in which a measurement of all relevant parameters of the material under identical measurement conditions is ensured, or at least made more probable.

An exemplary apparatus according to the present invention includes an optical measurement device for the simultaneous measurement of at least one optical parameter of the material to be tested.

This may permit a material sample to be measured at the same place and with the same modification, for example, with the same duration of effect of the relevant environmental parameter. Thus, the corresponding chemical conversion of the material sample may simultaneously be measured both electrically and optically. On the basis of the combination of the electrically and optically detected modification of the corresponding parameters, this may enable new statements to be made concerning the material to be tested, or concerning the corresponding chemical conversions of the material, which may result in a significant expansion of the knowledge concerning the corresponding chemical conversions of the material to be tested. This new knowledge may be advantageously used for the optimized further development of corresponding materials.

In addition, according to an exemplary embodiment of the present invention, the material sample may be tested and, if necessary, classified faster than in the prior art. In addition, an immediate comparison of the optical sensitivity of the material to be tested with its electrical sensitivity may be performed, so that additional statements concerning the material to be tested, or a selection with respect to the greater sensitivity of the material, may be made.

The measurement unit and the measurement apparatus may be situated in a common housing 4. This ensures, or at least increases the probability, of realizing a comparatively compact arrangement of the measurement unit with the measurement apparatus. This may result in an exemplary space-saving apparatus according to the present invention.

The modification of the electrical parameter and the modification of the optical parameter may be determined and evaluated at least depending on time, so that correspondingly generated parameter characteristics or curves may be compared. In this manner, a transition point, region or the like, of the chemical conversion occurring in the material due to the effect of the relevant environmental parameter, such as, for example, due to a charging with $CO_2$ of the material to be tested, may be determined.

In addition, various sensitivities of the electrical parameters and of the optical parameters may be determined more precisely on the basis of the characteristic of the determined parameter curves, which may be, for example, linear, potential, or exponential.

In developing an exemplary embodiment according to the present invention, the material to be tested is fashioned at least partially optically transparent. This permits, for example, using the optical measurement device, internal chemical conversions of the material to be measured. Materials such as electrically conductive polymers, for example, polythiophenes or the like, may be tested. In principle, materials that are both electrically conductive and optically transparent may be tested.

A measurement radiation of the measurement apparatus is provided depending on the optical transparency of the material to be tested. The measurement radiation may include, for example, infrared, visible, and/or ultraviolet radiation. If necessary, this may permit the testing, of numerous varying materials having a variety of optical properties or parameters.

In another exemplary embodiment according to the present invention, the measurement apparatus includes at least one sensor element for determining an intensity and/or a frequency range of the measurement radiation. For example, the optical measurement apparatus, such as, for example, a light-emitting diode or the like, may include a radiation source having a relatively narrow frequency band. For this purpose, a measurement of the intensity of the measurement radiation using a corresponding sensor element may determine the optical parameter or the modification thereof.

If necessary, a corresponding radiation source may emit a measurement radiation having a comparatively broad frequency band. In this case, the overall frequency band may be scanned using a scan unit, and the optical parameter or the modification thereof may be acquired.

The material to be tested may be situated on a substrate that is at least partially optically transparent. This enables the material to be tested to be situated on the substrate. In addition, this may permit an optical measurement to be realized via transmission of the measurement radiation. For example, the radiation source may be situated on one side of the substrate and the sensor element may be situated on the other side of the substrate, so that the measurement radiation transmits to both the material to be tested and to the at least partially optically transparent substrate.

Alternatively, the material to be tested may be situated on a substrate that is at least partially optically reflective. In this case, the optical measurement apparatus may be provided on the side of the substrate on which the material to be tested is situated. This may permit a compact exemplary apparatus according to the present invention and a comparatively simple mounting of the substrate, with the material sample to be tested located thereon, on a relatively simple place of deposit.

The material to be tested is penetrated twice due to the reflection at the at least partially optically reflective substrate, so that a higher degree of sensitivity of the material to be tested may be realized for the measurement of the optical parameter.

In yet another exemplary embodiment according to the present invention, at least one electrode, which is at least partially optically transparent, is provided. For example, in the above-described measurement of the optical parameter of the material to be tested by transmission of the measurement radiation, a corresponding electrode may enable a further optimization, since this permits the measurement radiation to penetrate one or more electrodes.

In still another exemplary embodiment according to the present invention, the at least partially optically transparent electrode is the material to be tested. In this manner, a second electrode, which may be necessary and comparatively expensive to realize, may become superfluous. This may, for example, reduce the expense of testing the material.

At least one electrode that is at least partially optically reflective is provided. In this manner, for example, the measurement of the optical parameter of the material to be tested, using reflection of the measurement radiation, may be improved in that the measurement radiation is reflected alternatively to, or in combination with, the reflection at the corresponding substrate, or is additionally reflected at the corresponding electrode that is at least partially optically reflective. This may improve the measurement of the optical parameter by reflection.

The measurement radiation of the measurement apparatus is provided depending on the optical transparency and/or reflection of the electrode and/or of the substrate. This may permit the measurement radiation to adapt to the electrodes or to the substrate.

Numerous different materials to be tested may be situated on the substrate. In this manner, for example, simultaneous testing of numerous materials of a wide variety may be performed, through which the development of corresponding sensor materials may be improved.

A classification of the materials or samples to be tested may be performed. In addition, using corresponding electronic evaluation units, an almost automatic testing and/or classification of the various materials or samples may be performed.

DETAILED DESCRIPTION

Figure 1:
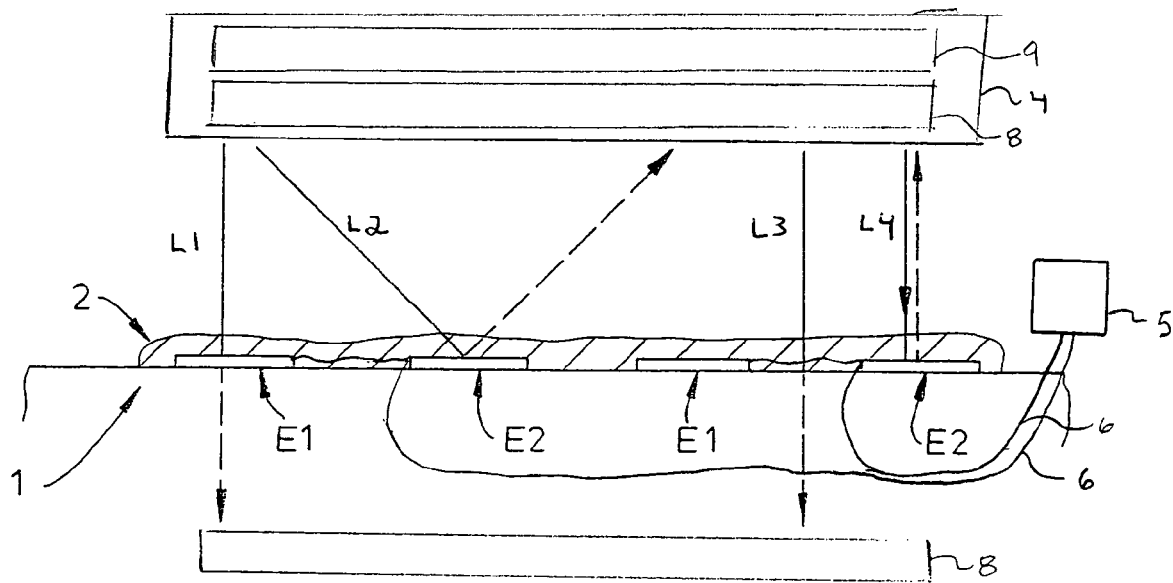
FIG. 1 is a schematic illustration showing details of an exemplary apparatus according to the present invention.

FIG. 1 shows a material 2 and two electrodes E1 and E2 on a substrate 1. Substrate 1 is at least partially transparent, for example, to accommodate a measurement radiation shown as beam L1, L2, L3, or L4. For example, with the use of visible or UV light, for example, glass or quartz may be used as the material for substrate 1, and with the use of infrared light, for example, silicon or sapphire may be used.

An indium-tin oxide electrode (ITO electrode) may, for example, be used as conductive and optically transparent electrodes E1 or E2, which may be sputtered onto substrate 1, if necessary, as an interdigital electrode structure. The interdigital electrode structure may have the shape of a double line of an electrode system. In this case, the lines or electrodes may be fashioned, for example, with a comb shape, the teeth of which mesh without touching one another.

The measurement of at least one electrical parameter of material 2 to be examined may occur, for example, via a current measurement, voltage measurement or resistance measurement between the two electrodes E1 or E2, using an electronic measurement unit 5 connected via lines 6.

In accordance with this exemplary embodiment of the present invention, beam L1, L2, L3, or L4 is generated and measured simultaneously during the electrical measurement, using an optical measurement device 7 which includes at least one radiation source 9 and a sensor element 8.

For exemplary purposes only, electrode E2 is shown as reflecting light beams L2 or L4. Light beams L2 or L4 penetrate material 2 twice, due to the reflection at electrode E2. As a result of a chemical conversion of material 2 due to a modification of an environmental parameter (not shown), for example, a charging with $CO_2$ of the apparatus, incident light beam L2 or L4, shown as a solid line, is changed to exiting light beam L2 or L4, shown as a broken line. In this case, beam L4 may be provided if material 2 is fluorescent.

The modification is measured by the sensor and is evaluated by an evaluation unit. Both an intensity and also a modification in the frequency spectrum of beams L1, L2, L3, or L4 may be acquired and evaluated.

For the measurement of beams L2 or L4, the optical sensor element 8 is situated on the side of substrate 1 on which the radiation source is located. This permits a comparatively compact exemplary apparatus according to the present invention. Substrate 2 need not be optically transparent. For example, substrate 2 may be fashioned as ceramic substrate 2 made of aluminum oxide or the like, or it may be fashioned in optically reflective fashion.

In another exemplary embodiment according to the present invention, in which beams L1 or L3 penetrate substrate 1 and material 2, the optical sensor element 8 is situated on the side of substrate 1 opposite the source of radiation. Given a transmission measurement according to light beam L1, for example, electrode E1 may be optically transparent. In this case, optically transparent electrode E1 may be made of electrically conductive polymers or the like.

Figure 2:
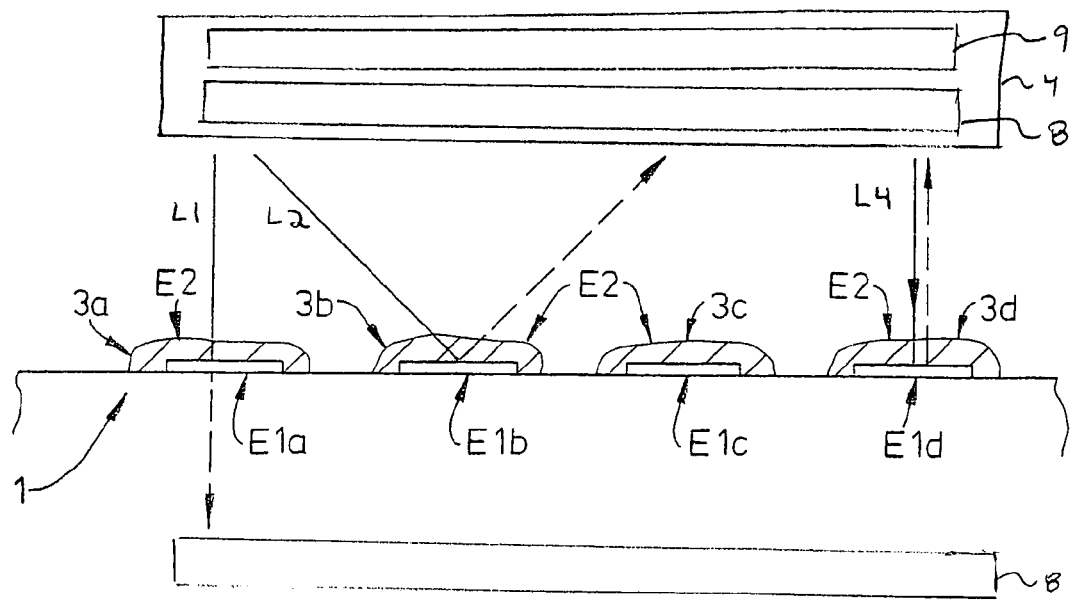
FIG. 2 is a schematic illustration showing details of another exemplary apparatus according to the present invention.

FIG. 2 shows yet another exemplary apparatus according to the present invention. In this exemplary embodiment, elements comparable to the elements according to the exemplary embodiment described above with reference to FIG. 1 have the same reference characters.

In contrast to the apparatus described above with reference to FIG. 1, in the exemplary apparatus according to FIG. 2, the material to be tested is fashioned as a material 3 that does not connect the electrode fingers E1, whereby this material is simultaneously applied to electrode E1, as second electrode E2. For example, material 3 may be merged at a suitable point on substrate 1. Alternatively, for example, four different materials 3a, 3b, 3c, 3d may be applied on four different electrodes E1a, E1b, E1c, E1d.

Numerous varying material samples 2, 3 may be applied together onto a substrate 1. For example, a matrix-type arrangement of widely varying material samples 2, 3 may be provided.

What is claimed is:

1. An apparatus for testing a material, comprising:
   a measurement unit for measuring at least one electrical parameter of the material;
   an optical measurement apparatus for a simultaneous measurement of at least one optical parameter of the material;
   at least one electrode that is at least partially optically transparent;
   wherein the material includes the at least one electrode that is at least partially optically transparent.

2. The apparatus according to claim 1, wherein the measurement unit and the optical measurement apparatus are situated in a common housing.

3. The apparatus according to claim 1, wherein the material is at least partially optically transparent.

4. The apparatus according to claim 1, wherein a measurement radiation of the optical measurement apparatus is provided depending on an optical transparency of the material.

5. The apparatus according to claim 4, wherein the measurement radiation includes at least one of infrared radiation, visible radiation and ultraviolet radiation.

6. The apparatus according to claim 4, wherein the optical measurement apparatus includes at least one sensor element for determining at least one of an intensity and a frequency range of the measurement radiation.

7. The apparatus according to claim 1, wherein the material is situated on a substrate that is at least partially optically transparent.

8. The apparatus according to claim 1, wherein the material is situated on a substrate that is at least partially optically reflective.

9. The apparatus according to claim 1, further comprising:
   at least one electrode that is at least partially optically reflective.

10. The apparatus according to claim 1, wherein a measurement radiation of the measurement apparatus is provided depending on at least one of an optical transparency of at least one electrode, an optical reflection of the at least one electrode, an optical transparency of a substrate, and an optical reflection of the substrate.

11. An apparatus for testing a material, comprising:
    a measurement unit for measuring at least one electrical parameter of the material; and
    an optical measurement apparatus for a simultaneous measurement of at least one optical parameter of the material;
    wherein the material includes a plurality of different materials, the plurality of different materials being situated on a substrate.

12. The apparatus according to claim 11, further comprising:
    at least one electrode that is at least partially optically transparent.

13. The apparatus according to claim 11, wherein the measurement unit and the optical measurement apparatus are situated in a common housing.

14. The apparatus according to claim 11, wherein the material is at least partially optically transparent.

15. The apparatus according to claim 11, wherein a measurement radiation of the optical measurement apparatus is provided depending on an optical transparency of the material.

16. The apparatus according to claim 15, wherein the measurement radiation includes at least one of infrared radiation, visible radiation and ultraviolet radiation.

17. The apparatus according to claim 15, wherein the optical measurement apparatus includes at least one sensor element for determining at least one of an intensity and a frequency range of the measurement radiation.

18. The apparatus according to claim 11, wherein the material is situated on a substrate that is at least partially optically transparent.

19. The apparatus according to claim 11, wherein the material is situated on a substrate that is at least partially optically reflective.

20. The apparatus according to claim 11, further comprising:
    at least one electrode that is at least partially optically reflective.

21. The apparatus according to claim 11, wherein a measurement radiation of the measurement apparatus is provided depending on at least one of an optical transparency of at least one electrode, an optical reflection of the at least one electrode, an optical transparency of a substrate, and an optical reflection of the substrate.

22. A method for testing a material, comprising:
    measuring an electrical parameter of the material; and
    simultaneously measuring an optical parameter of the material;
    wherein the material includes a plurality of different materials, the plurality of different materials being situated on a substrate.

23. The method according to claim 22, wherein the optical parameter of the material is measured in the measuring step with a sensor.

* * * * *